United States Patent
German et al.

(10) Patent No.: US 7,291,174 B2
(45) Date of Patent: Nov. 6, 2007

(54) PROSTHETIC TIBIAL COMPONENT WITH MODULAR SLEEVE

(75) Inventors: Deborah S. German, Plymouth, IN (US); Todd D. Durniak, Ft. Wayne, IN (US); Danny W. Rumple, Warsaw, IN (US); Christel M. Klebba, Columbia City, IN (US)

(73) Assignee: Depuy Products, Inc., Warsaw, IN (US)

( * ) Notice: Subject to any disclaimer, the term of this patent is extended or adjusted under 35 U.S.C. 154(b) by 221 days.

(21) Appl. No.: 10/641,752

(22) Filed: Aug. 15, 2003

(65) Prior Publication Data

US 2004/0049286 A1   Mar. 11, 2004

Related U.S. Application Data

(60) Provisional application No. 60/409,284, filed on Sep. 9, 2002.

(51) Int. Cl.
   *A61F 2/38*   (2006.01)
(52) U.S. Cl. .............................. 623/20.15; 623/20.33; 623/23.46
(58) Field of Classification Search .. 623/20.14–20.16, 623/20.21, 20.28–20.34, 23.46
   See application file for complete search history.

(56) References Cited

U.S. PATENT DOCUMENTS

| 4,634,444 A | 1/1987 | Noiles |
| 4,888,021 A | 12/1989 | Forte |
| 4,944,757 A | 7/1990 | Martinez |
| 5,011,496 A | 4/1991 | Forte |
| 5,152,797 A * | 10/1992 | Luckman et al. ........ 623/20.16 |
| 5,356,414 A | 10/1994 | Cohen |
| 5,480,445 A | 1/1996 | Burkinshaw |
| 6,053,945 A * | 4/2000 | O'Neil et al. ............ 623/20.32 |
| 6,506,216 B1 | 1/2003 | McCue |

FOREIGN PATENT DOCUMENTS

| EP | 0 538 987 B1 | 4/1993 |
| EP | 0 904 749 A2 | 3/1999 |
| EP | 0 904 749 A3 | 5/2000 |

* cited by examiner

*Primary Examiner*—David H. Willse

(57) ABSTRACT

A prosthetic knee system has a tibial component and a modular sleeve. The tibial component has a tibial tray, a stem and keels extending between the distal surface of the tray and the stem. The modular sleeve has an oval proximal surface with spaced reliefs. The reliefs and keels are sized, shaped and positioned to allow the modular sleeve to be mounted on the tibial component with the stem of the tibial component received in the interior channel of the sleeve and the keels of the tibial component received in the spaced reliefs of the modular sleeve, and to allow for some relative rotation between the tibial component and the sleeve. The system gives the surgeon the freedom to implant the tibial component alone, with the keels providing stability, or, in the case of bone deficiency, to implant the tibial component and sleeve as an assembly.

18 Claims, 9 Drawing Sheets

PROSTHETIC TIBIAL COMPONENT WITH MODULAR SLEEVE

This application claims the benefit of U.S. Provisional Application No. 60/409,284, filed on Sep. 9, 2002, by Deborah S. German, Todd D. Durniak, Danny W. Rumple and Christel M. Klebba and entitled "Prosthetic Tibial Component with Modular Sleeve," which is incorporated by reference herein in its entirety.

BACKGROUND OF THE INVENTION

The present invention relates to modular components of a prosthetic joint, and more particularly to modular components of a prosthetic knee joint.

The knee joint basically consists of the bone interface of the distal end of the femur and the proximal end of the tibia. Appearing to cover or at least partially protect this interface is the patella which is a sesamoid bone within the tendon of the long muscle (quadriceps) on the front of the thigh. This tendon inserts into the tibial tuberosity and the posterior surface of the patella is smooth and glides over the femur.

The femur is configured with two knob-like processes (the medial condyle and the lateral condyle) which are substantially smooth and articulate with the medial plateau and the lateral plateau of the tibia, respectively. The plateaus of the tibia are substantially smooth and slightly cupped thereby providing a slight receptacle for receipt of the femoral condyles.

When the knee joint is injured whether as a result of an accident or illness, a prosthetic replacement of the damaged joint may be necessary to relieve pain and to restore normal use to the joint. Typically the entire knee joint is replaced by means of a surgical procedure which involves removal of the ends of the corresponding damaged bones and replacement of these ends with prosthetic implants. This replacement of a native joint with a prosthetic joint is referred to as a primary total-knee arthroplasty.

On occasion, the primary knee prosthesis fails. Failure can result from many causes, including wear, aseptic loosening, osteolysis, ligamentous instability, arthrofirosis and patellofemoral complications. When the failure is debilitating, revision knee surgery may be necessary. In a revision, the primary knee prosthesis is removed and replaced with components of a revision prosthetic knee system.

In revision knee surgery or arthroplasty, bone loss on the proximal tibia can make it difficult to properly stabilize the tibial component of the revision system with respect to the intramedullary canal of the tibia. Various implant configurations are available for immobolization and stabilization of the tibial component, and for distributing the load at the proximal end of the tibia.

For example, it is known to provide integral keels that extend from the stem of the tibial component to the distal surface of the tibial tray. Such a prosthetic implant is illustrated in FIG. 1. As there shown, the tibial component 10 includes a tibial tray 12 and a tibial stem 14 extending outward from and integral with the distal side 16 of the tibial tray 12. In this prior art component, three integral keels 18, 20, 22 extend between the stem 14 and the distal surface 16 of the tray 12. The stem is hollow and can accept a stem extension (not shown) at its distal end 24. The keels 18, 20, 22 serve to help stabilize the implant 10 in the proximal tibia.

It is also known to provide a stepped or terraced sleeve for the tibial stem. Such sleeves are sold commercially as "S-ROM" products by DePuy Orthopaedics, Inc. of Warsaw, Ind. An example of such a system is illustrated in FIGS. 2-5 of the drawings. The tibial component 30 of this prior art system also has a tibial tray 32 and an integral stem 34 that can be connected to stem extensions (not shown) at the distal end 38. However, in this prior art system, there are no keels on the distal side 36 of the tibial tray 32. In this prior art system, a separate, modular sleeve is provided. An example of such a modular sleeve is illustrated in FIGS. 2-4. The modular sleeve is shown at 40 in FIGS. 2-4. The modular sleeve 40 has a tapered interior bore 42 that in which part of the stem 34 of the tibial component 40 of FIG. 5 is received. The tapered interior bore 42 is widest at the proximal end and most narrow at the distal end, corresponding to the shape of the stem 34. As shown in FIGS. 2 and 3, the proximal surface 44 of the modular sleeve 40 has an overall elliptical shape and is generally flat to fit against the distal surface 36 of the tibial tray 32. As shown in FIG. 4, the modular sleeve has a stepped or terraced outer surface 46. The sleeves help stabilize the implant, particularly in case of bone loss, and distribute load.

SUMMARY OF THE INVENTION

The present invention provides a modular prosthetic implant system that provides the surgeon and patient with the advantages of both a keeled tibial component and a modular sleeve design, increasing the surgeon's options during surgery so that the optimal implant design can be selected for the patient's needs.

In one aspect, the present invention provides a modular prosthetic tibial sleeve comprising a proximal surface having a generally oval outline with spaced reliefs. The sleeve also has a distal end and a terraced outer surface tapering from the proximal surface toward the distal end. The sleeve has an interior channel extending from the proximal surface to the distal end.

In another aspect, the present invention provides a prosthetic knee system comprising a femoral component, a tibial component comprising a tibial tray, a stem and a keel, a tibial bearing component, and a modular sleeve. The tibial tray has a distal side and an opposite side. The stem extends from the distal side of the tray and the keel extends between the distal side of the tray and the stem. A majority of the opposite side of the tibial tray is planar. The tibial bearing component has a contoured bearing side. The modular sleeve comprises a proximal surface with a relief, a distal end, a tapered outer surface between the proximal surface and the distal end and an interior channel extending from the proximal surface to the distal end. The keel and stem of the tibial component and interior channel and relief of the modular sleeve are sized, shaped and positioned to allow the modular sleeve to be mounted on the tibial component with at least a portion of the stem of the tibial component received in the interior channel of the sleeve and at least a portion of the keel of the tibial component received in the relief of the modular sleeve. The stem of the tibial component and interior channel of the sleeve are sized and shaped to allow the tibial component and modular sleeve to be selectively locked together through friction to prevent rotation between the tibial component and the sleeve. The keel and the relief are sized, shaped and positioned to allow the tibial component and the sleeve to be selectively locked together in one of a plurality of orientations.

DETAILED DESCRIPTION OF THE INVENTION

Figure 1:
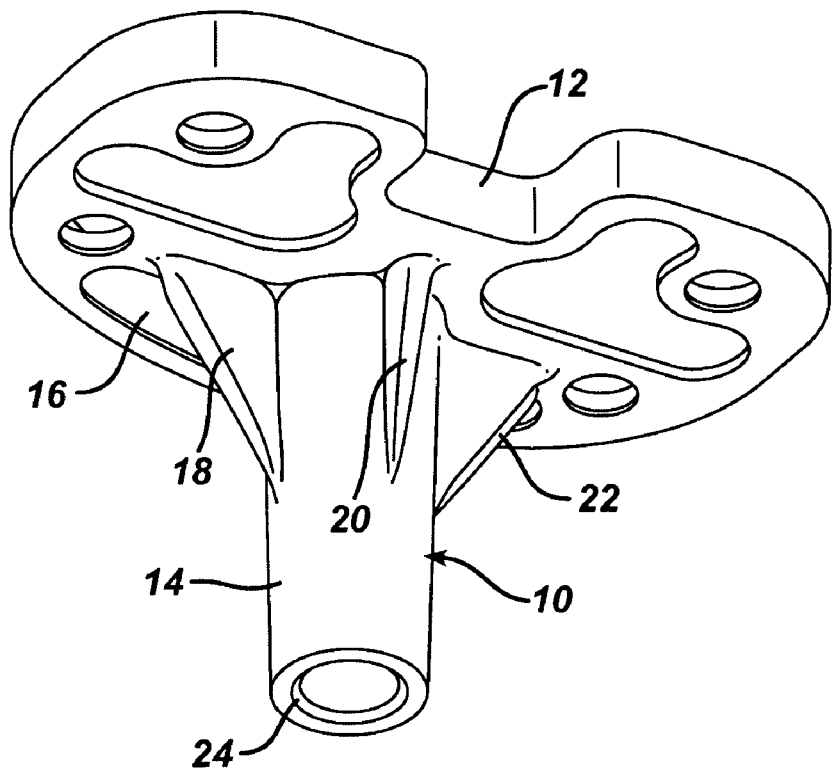
FIG. 1 is a perspective view of a prior art tibial implant with keels.
Figure 2:
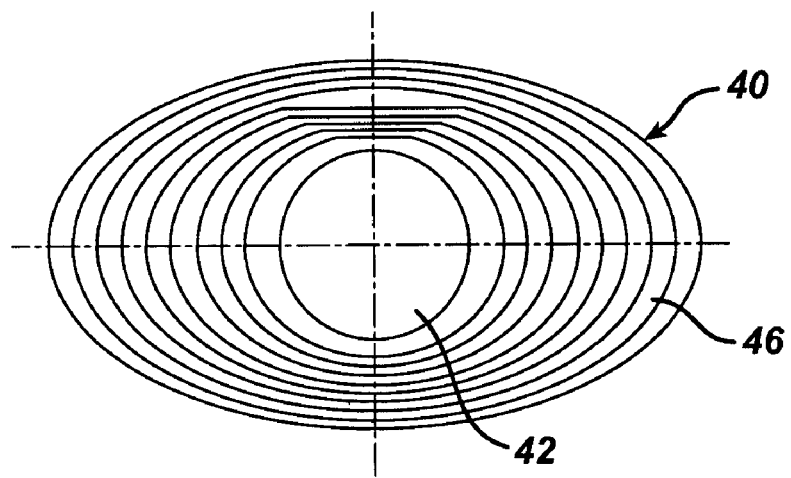
FIG. 2 is a bottom plan view of a prior art terraced sleeve.
Figure 3:
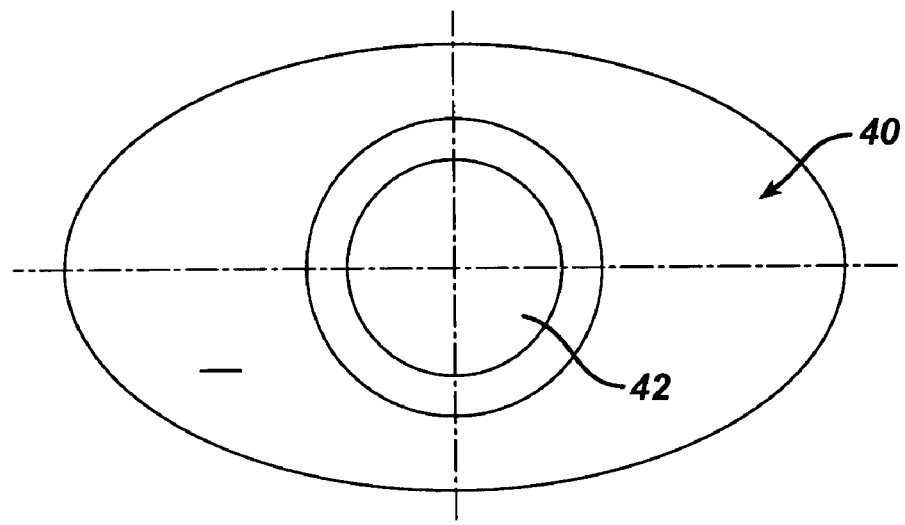
FIG. 3 is a top plan view of the prior art terraced sleeve of FIG. 2.
Figure 4:
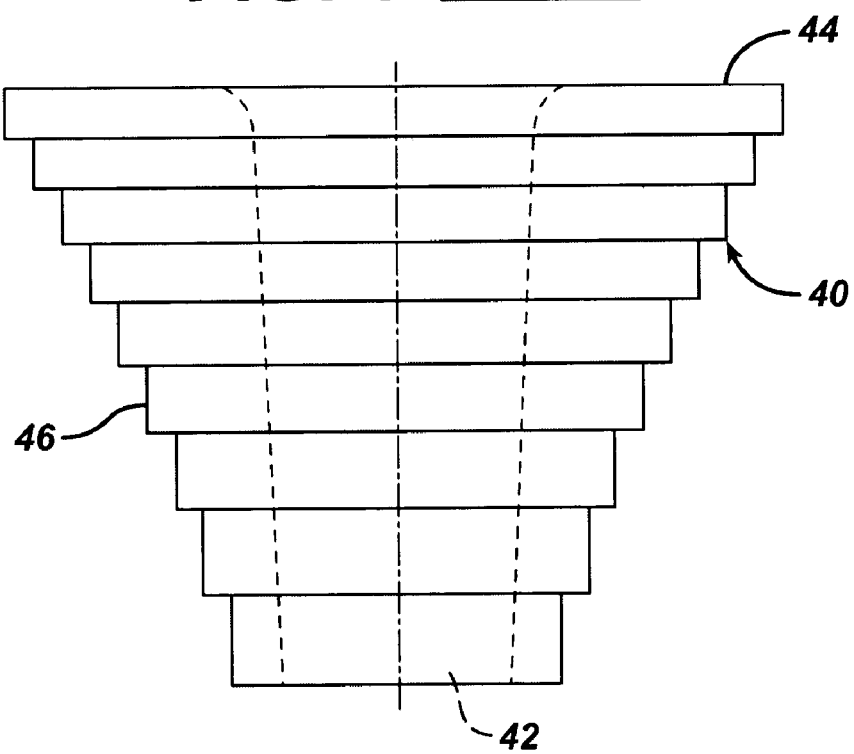
FIG. 4 is a front elevation of the prior art terraced sleeve of FIGS. 2-3.
Figure 5:
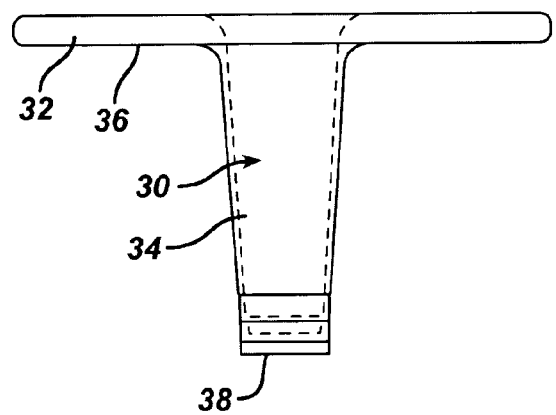
FIG. 5 is a front elevation of a prior art tibial implant for use with the prior art terraced sleeves of FIGS. 2-4.
Figure 6:
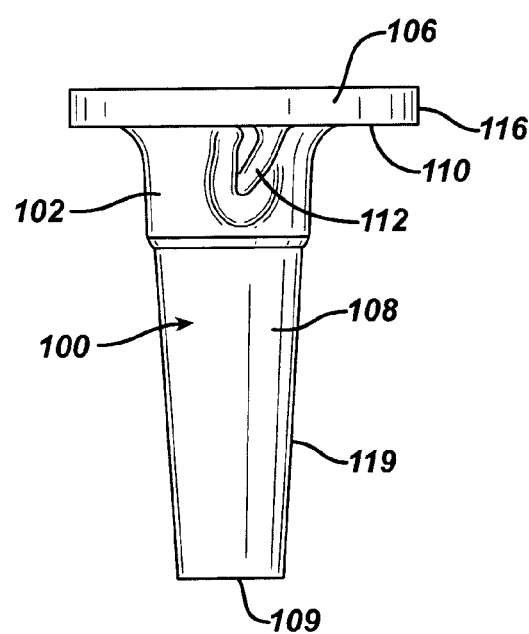
FIG. 6 is a side elevation of a tibial component of the implant system of the present invention.
Figure 7:
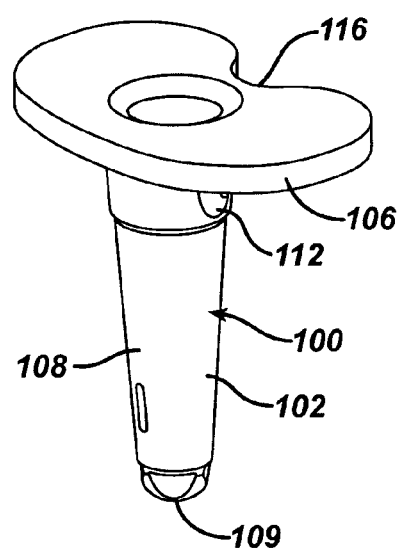
FIG. 7 is a perspective view of the tibial component of FIG. 6.
Figure 8:
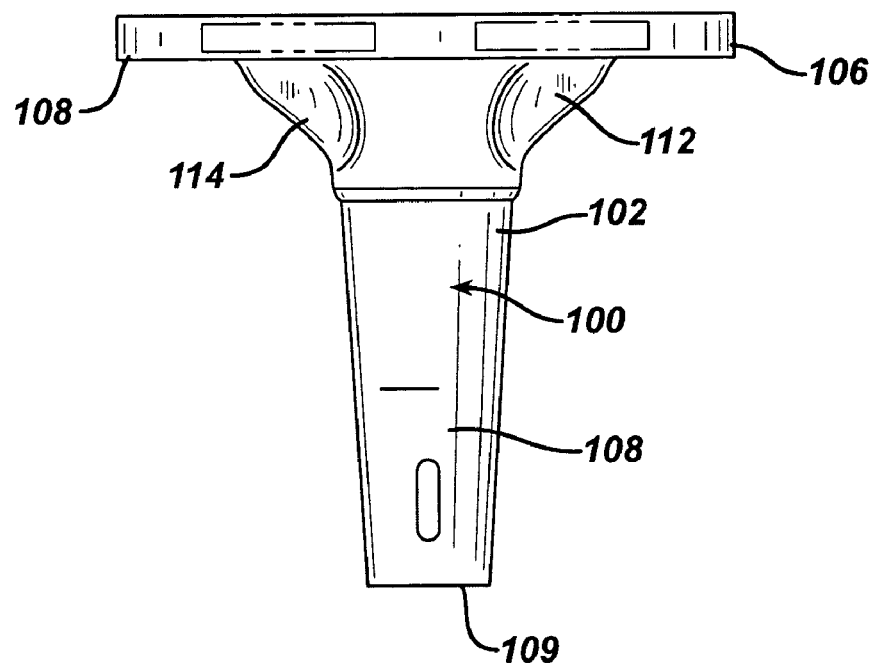
FIG. 8 is a front elevation of the tibial component of FIGS. 6-7.

An example of a prosthetic knee implant system 100 embodying the principles of the present invention is illustrated in FIGS. 6-22. The illustrated implant system 100 includes a tibial component 102 and a modular sleeve 104. The tibial component 102 and modular sleeve 104 can be provided as components of a prosthetic knee implant system that also includes a femoral component and tibial bearing. An example of a femoral component is illustrated at 103 in FIG. 21 and an example of a tibial bearing insert is illustrated at 105 in FIG. 22. It should be understood that these illustrated components 103, 105 are provided as examples of components that can be used with the tibial component 102 and modular sleeve 104 shown in FIGS. 6-20. The present invention is not limited to the particular femoral and tibial bearing insert components 103, 105 illustrated or the illustrated features of these components unless expressly called for in the claims.

The tibial component 102 of the illustrated system 100 includes a tibial tray 106 and an integral stem 108 extending distally from the distal side 110 of the tibial tray 106. Two keels 112, 114 are integral with and connect the tibial tray 106 and the stem 108. In the illustrated embodiment, the two keels 112, 114 extend outward and toward the posterior side 116 of the tray 106, defining an angle of 130°, as shown at θ in FIG. 9. However, it should be understood that this particular keel configuration is provided by way of example only; the invention is not limited to any particular number or geometric relationship between the keels unless expressly called for in the claims; for example, the tibial component could have three or more keels.

Figure 9:
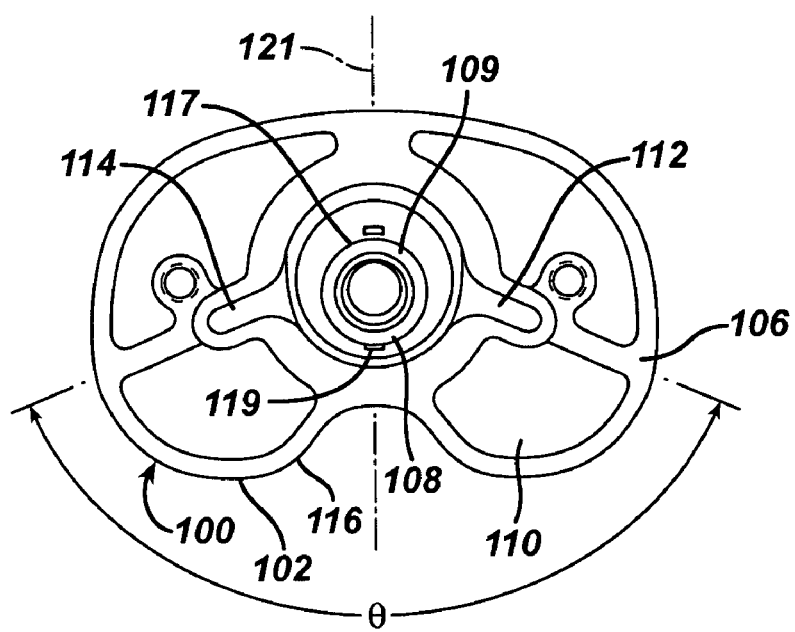
FIG. 9 is a bottom plan view of the tibial component of FIGS. 6-8.

As shown in FIG. 9, the illustrated tibial component is symmetrical about a central plane 121 that divides the tibial tray 106 into medial and lateral portions.

The stem 108 is tapered from a widest dimension at the tibial tray 106 to a most narrow dimension at the distal end 109 of the stem 108. The stem has an anterior side 117 and posterior side 119. The central stem 108 has a Morse taper.

Figure 10:
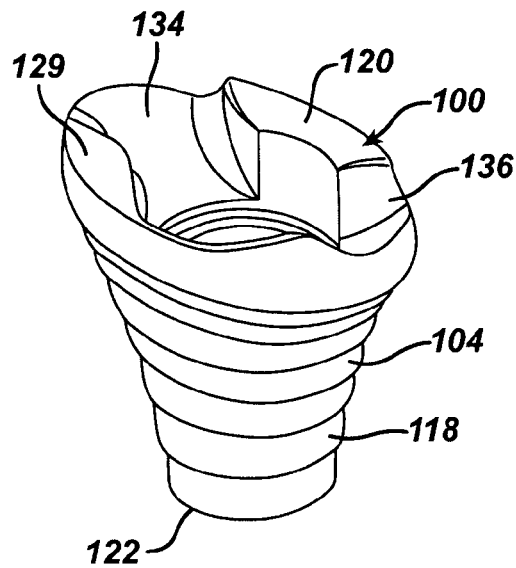
FIG. 10 is a perspective view of a modular sleeve of the implant system of the present invention.
Figure 11:
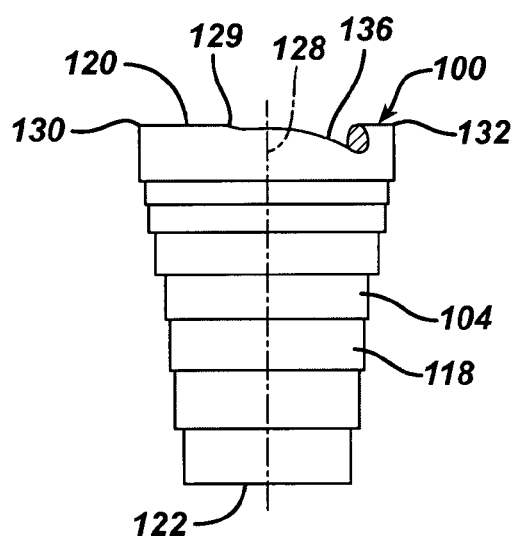
FIG. 11 is a side elevation of the modular sleeve of FIG. 10.
Figure 13:
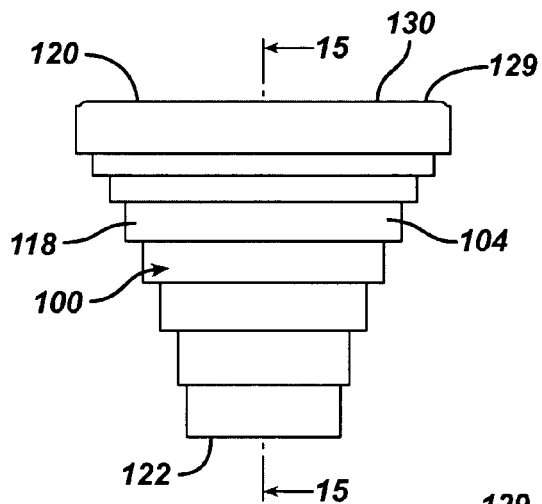
FIG. 13 is a front elevation of the modular sleeve of FIGS. 10-12.
Figure 14:
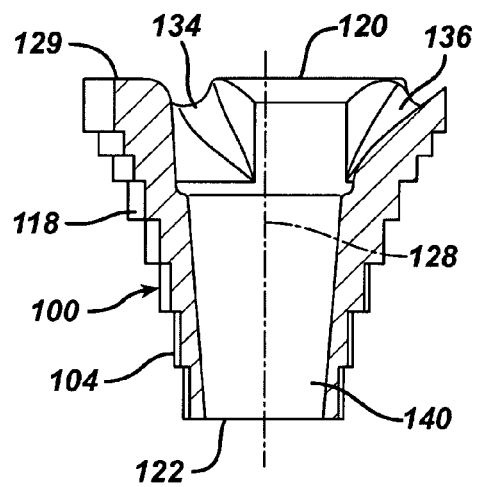
FIG. 14 is a cross-section of the modular sleeve of FIGS. 10-13, taken along line 14-14 of FIG. 12.
Figure 15:
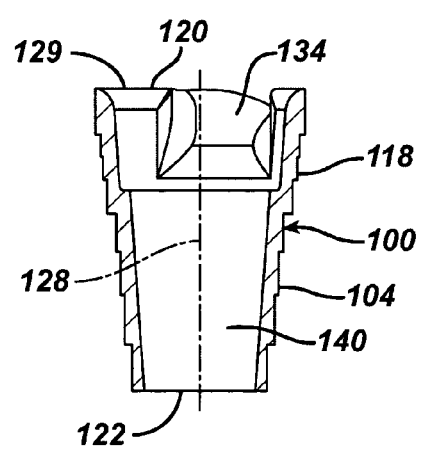
FIG. 15 is a cross-section of the modular sleeve of FIGS. 10-14, taken along line 15-15 of FIG. 13.

As shown in FIGS. 10-11 and 13, the illustrated modular sleeve 104 has a stepped or terraced outer surface 118, tapering with each step from the proximal end 120 to the distal end 122. This terraced surface 118 serves the same function as the terraced surface of the prior art modular sleeve: it helps to stabilize the implant in the tibia, particularly in the case of bone loss, and to distribute load in the tibia. However, the invention is not limited to the illustrated configuration unless expressly called for in the claims.

Figure 12:
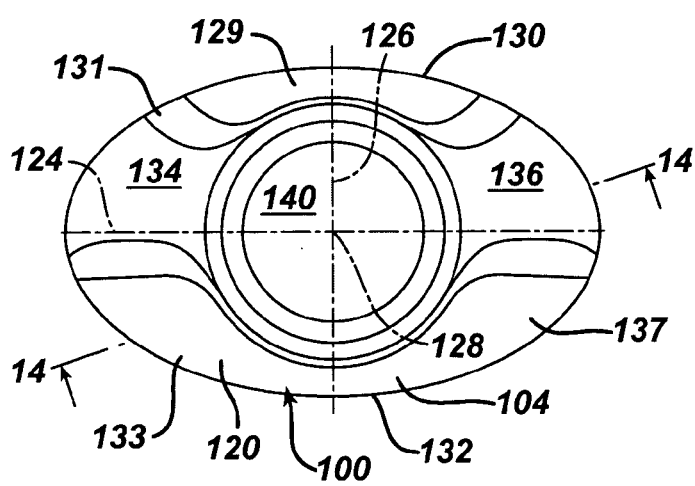
FIG. 12 is a top plan view of the modular sleeve of FIGS. 10-11.

As shown in the top plan view of FIG. 12, the modular sleeve 104 of the illustrated embodiment has an overall elliptical outline, with a major axis 124 and a minor axis 126, and a central longitudinal axis 128. It has proximal surface 129 with a posterior-facing edge 130 and an anterior-facing edge 132. The major axis 124 defines a posterior portion 131 and an anterior portion 133 of the proximal surface (shown in FIGS. 12 and 16).

Figure 16:
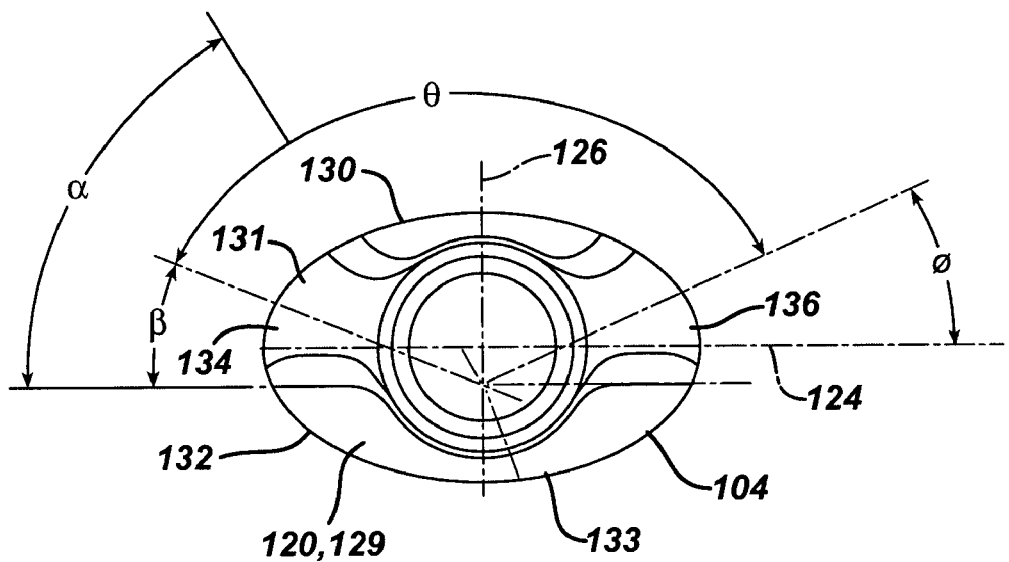
FIG. 16 is a top plan view of the modular sleeve of FIGS. 10-15 showing the angular relationships and clearance allowed by the reliefs of the modular sleeve.
Figure 17:
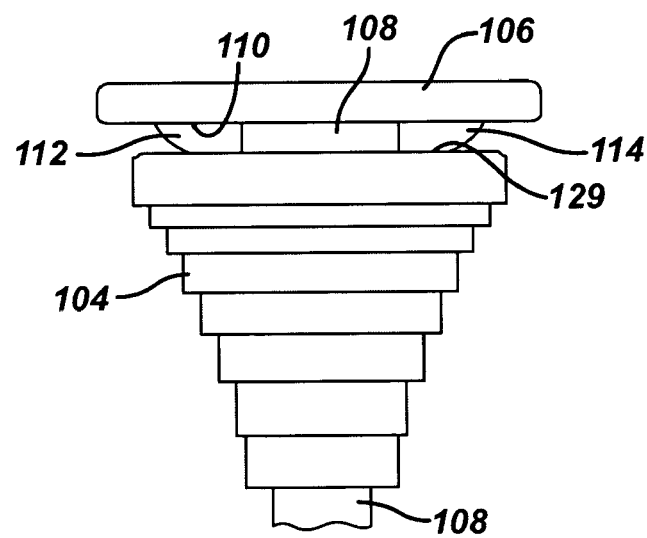
FIG. 17 is a front elevation of an assembly of a modular sleeve and tibial component.

The proximal surface 129 has an overall oval outline in top plan view. As shown in FIGS. 12 and 16, the modular sleeve 104 of the illustrated embodiment includes two reliefs 134, 136 in the proximal surface 129, generally in the posterior portion 131 between the major axis 124 and the posterior-facing edge 132 of the modular sleeve 104. These reliefs 134, 136 are shaped to receive the two keels 112, 114 of the tibial component 110 so that the modular sleeve can be used with the keeled tibial component.

The two reliefs 134, 136 are shaped to allow some relative rotation between the tibial component 110 and the sleeve 104 when the tibial component 110 and sleeve 104 are assembled. FIG. 16 illustrates the angular relationships of various structures of the sleeve 104. In the illustrated embodiment, the angle α is 56°, β is 25°, θ is 130° to correspond with the angle θ between the keels 112, 114 as shown in FIG. 9, and Φ is 25°. With these angular relationships, the shapes of the keels 112, 114 and reliefs 134, 136 in the illustrated embodiment will allow for about plus or minus 20° relative rotation between these components 104, 110 in assembly. However, it should be understood that these angles are provided as examples only; the present invention is not limited to any particular angular relationship unless expressly set forth in the claims. In addition, the present invention is not limited to any particular degree of relative movement allowed between the components unless expressly called for in the claims. It should be understood that the particular shape and geometric relationship between the reliefs 134, 136 are provided by way of example only; the present invention is not limited to the structure described and illustrated unless expressly called for in the claims.

The modular sleeve 104 also has an interior channel 140 that extends from the proximal surface 129 to the distal end 122 of the sleeve 104. The interior channel 140 is shaped to receive and frictionally interlock with the stem 108 of the tibial component 110 when the sleeve 104 and tibial component 110 are assembled and impacted together. The interior channel 140 tapers from a largest diameter at the proximal surface 129 to a smallest diameter at the distal end 122. The tapers of the interior channel 140 and stem 108 are Morse tapers. Once the stem 108 and sleeve 104 frictionally interlock, there is no longer any relative rotation or longitudinal movement between the stem 108 and sleeve 104.

The components of the system of the present invention may be made out of standard materials for such prosthetic implants. For example, the modular sleeve may be made out of a titanium alloy or a cobalt chrome alloy, and the tibial component can be made also be made out of a titanium or cobalt chrome alloy. However, it should be understood that the present invention is not limited to any particular material unless expressly called for in the claims.

The system of the present invention may be provided with the features disclosed in the following U.S. provisional patent applications filed on Sep. 9, 2002: application Ser. No. 60/409,319, entitled "UNIVERSAL TIBIAL AUGMENT," filed by Deborah S. German and Jeffery L. Koenemann (DEP 798); and application Ser. No. 60/409,262, entitled "DUO-FIXATION PROSTHIC JOINTS" filed by Brian Haas (DEP 799). These provisional applications are incorporated by reference herein in their entireties. The United States patent applications filed concurrently herewith based upon and claiming priority to these provisional patent applications are also incorporated by reference herein in their entireties.

To use the system of the present invention, the surgeon prepares the patient and performs standard surgical techniques to prepare the bone to receive the tibial component 110. For example, the surgeon may progressively ream the intramedullary canal of the tibia to receive the stem 108 and an appropriately sized stem extension (not shown). Trialing may be done in a standard manner. During the procedure, the surgeon determines if the condition of the patient's proximal tibia is suitable for use of the tibial component 110 alone without the sleeve 104. If the proximal tibia has adequate healthy bone tissue, the surgeon can implant the tibial component 110 in a standard manner, and the interaction of the keels 112, 114 and the patient's bone tissue should stabilize the tibial component 110 in the bone. If the surgeon determines that there is a cavitary defect or inadequate healthy bone tissue in the proximal tibia, the surgeon can prepare the proximal tibia to receive the assembly of the tibial component and the sleeve using standard reamers and broaches. The surgeon can then insert the stem 108 through the channel 140 of the sleeve 104 and move them together until the keels 112, 114 are received in the reliefs 134, 136 of the sleeve. The modular assembly of the tibial component 110 and sleeve 104 can then be implanted in a standard manner. Impaction of the assembly 110, 104 should interlock the components 110, 104 together. The surgeon can perform other standard techniques to complete the preparation of the femur.

Figure 18:
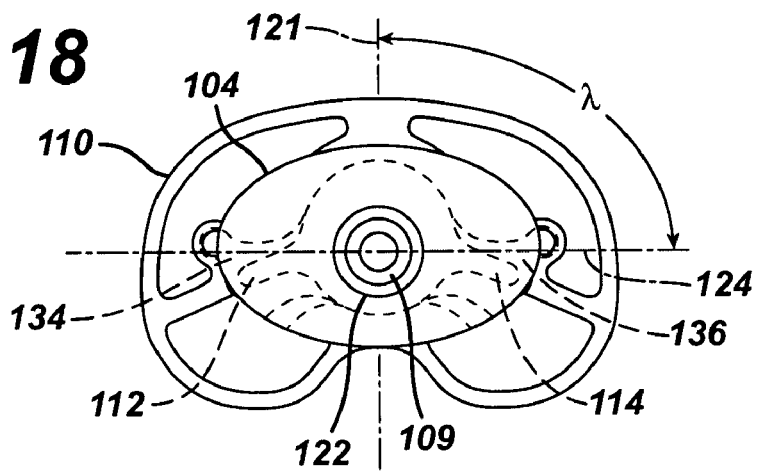
FIG. 18 is a bottom plan view of the assembly of the modular sleeve and tibial component, with parts removed for clarity of illustration, showing one possible angular relationship between the tibial component and the sleeve.
Figure 19:
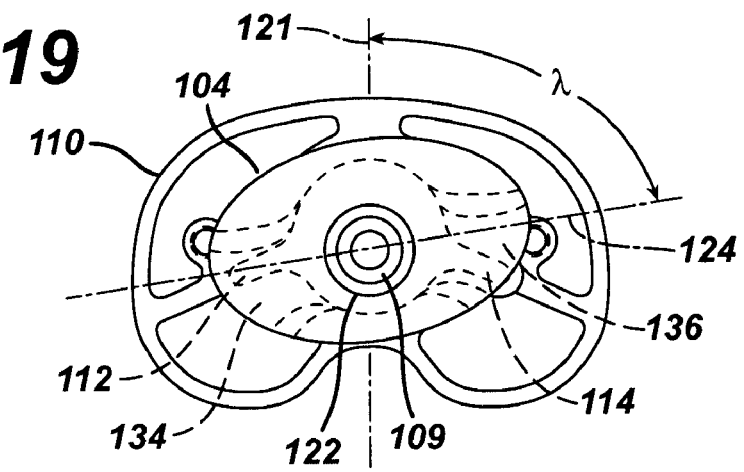
FIG. 19 is a bottom plan view of the assembly of the modular sleeve and tibial component, with parts removed for clarity of illustration, showing a second possible angular relationship between the tibial component and the sleeve.
Figure 20:
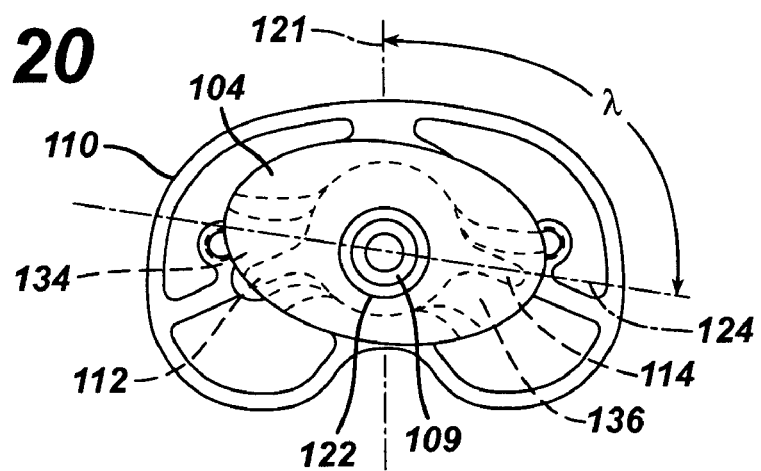
FIG. 20 is a bottom plan view of the assembly of the modular sleeve and tibial component, with parts removed for clarity of illustration, showing a third possible angular relationship between the tibial component and the sleeve.

The modular assembly of the tibial component 110 and the sleeve 104 is illustrated in FIGS. 17-20. The design of the reliefs 134, 136 in the present invention allows for some independent positioning of the sleeve 104 and the tibial component 110, as shown in FIGS. 18-20. The surgeon can place the sleeve 104 in an optimal position for stabilizing the implant while also setting the tibial component 110 in the proper position for interaction with the femoral component 103 of the implant system. For example, as shown in FIG. 18, the sleeve 104 and be placed on the tibial component such that the keels 112, 114 are substantially centered in the reliefs 134, 136; in this configuration, the angle λ between the central plane 121 of the tibial tray and a plane through the major axis 124 of the sleeve 104 can vary: in FIG. 18, the angle λ is 90°. The keels can also be off-center in the reliefs, as shown in FIGS. 19 and 20: in FIG. 19, the angle λ is 70°; and in FIG. 20 the angle λ is 110°. Thus, the illustrated embodiment of the invention allows the surgeon to rotate the tibial component and sleeve about the interior channel 140 of the sleeve, with a latitude of +/−20°. It should be understood that these angles are provided as examples only; the present invention is not limited to these angles or to any particular degree of freedom unless expressly called for in the claims.

Once the optimal relative rotational position is selected, the surgeon can interlock the tibial component 102 and the sleeve 104 in this optimal position by impacting the components to frictionally engage the stem 108 and the interior surface of the sleeve 104 that defines the interior channel 140. Thus, the tibial component 102 and sleeve 104 can be locked in a variety of relative positions, such as the positions illustrated in FIGS. 18-20.

It will be appreciated by those in the art that different sizes of tibial components 110 and sleeves 104 can be provided in a single surgical kit for use by the surgeon.

Figure 21:
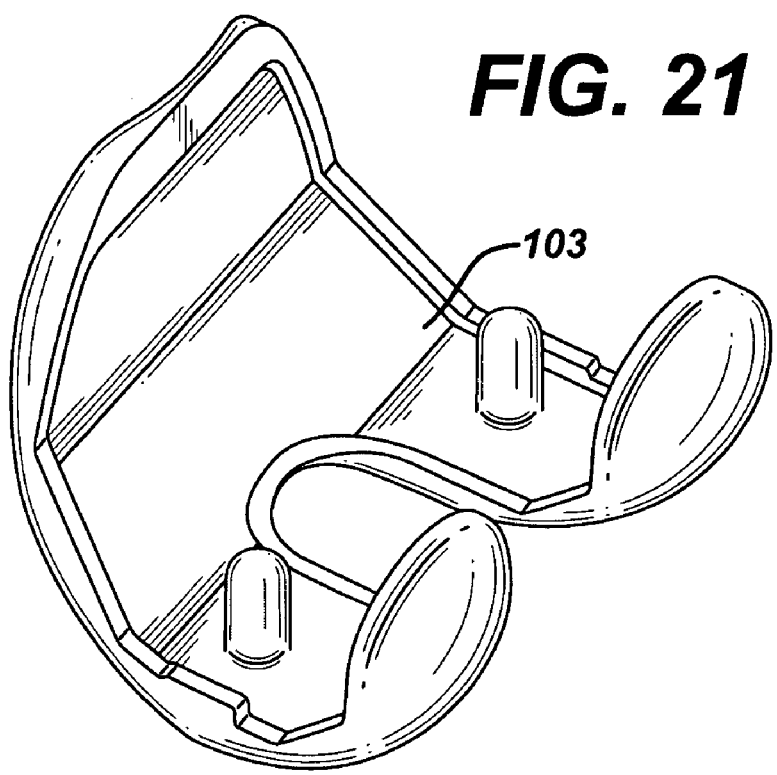
FIG. 21 is a perspective view of an example of a femoral component that could be used as part of a prosthetic knee system with the modular sleeve and tibial component of FIGS. 6-20.
Figure 22:
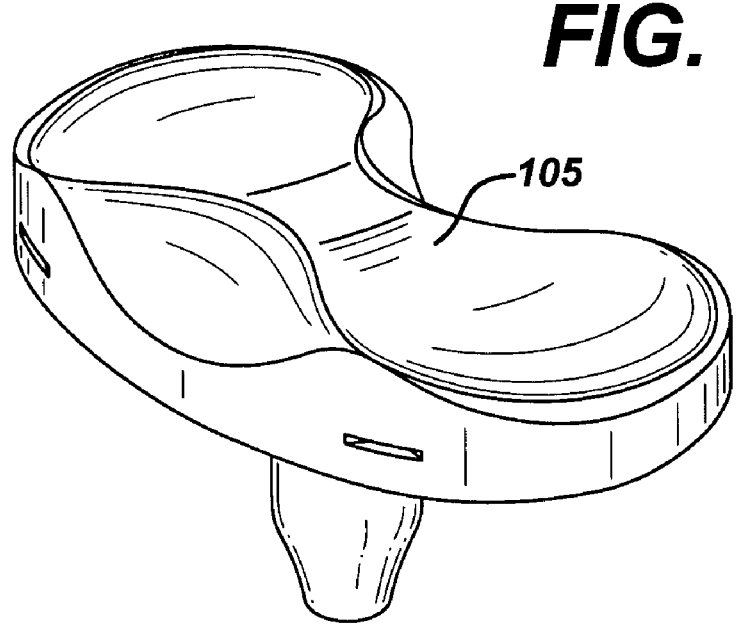
FIG. 22 is a perspective view of an example of a tibial bearing component that could be used as part of a prosthetic knee system with the modular sleeve and tibial component of FIGS. 6-20 and the femoral component of FIG. 21.

It will also be appreciated by those in the art that the illustrated tibial component would be used in conjunction with a tibial bearing insert such as that illustrated at 105 in FIG. 22 and with a femoral component such as that illustrated at 103 in FIG. 21.

Although the invention has been illustrated for use in a prosthetic knee system, and more particularly for use with the tibial components of a prosthetic knee system, it should be appreciated that the principles of the present invention may be applicable to other prosthetic joints. Moreover, while the illustrated embodiment of the invention may be particularly useful in revision surgery, the principles of the present invention may also find application in primary joint arthroplasties.

While only a specific embodiment of the invention has been described and shown, it is apparent that various alternatives and modifications can be made thereto. Moreover, those skilled in the art will also recognize that certain additions can be made to these embodiments. It is, therefore, the intention in the appended claims to cover all such alternatives, modifications and additions as may fall within the true scope of the invention.

We claim:

1. A prosthetic knee system comprising:
    a tibial component comprising a tibial tray, a stem and a keel, the tibial tray having a distal side and an opposite side, the stem extending from the distal side of the tibial tray, the keel extending between the distal side of the tray and the stem, a majority of the opposite side of the tibial tray being planar; and
    a modular sleeve comprising a proximal surface with a relief, a distal end, a terraced outer surface between the proximal surface and the distal end and an interior channel extending from the proximal surface to the distal end, the outer surface tapering from the proximal surface toward the distal end and the interior channel being sized and shaped to receive at least a portion of the stem of the tibial component;

wherein the keel, stem, interior channel and relief are sized, shaped and positioned to allow the sleeve to be mounted on the tibial component with at least a portion of the stem of the tibial component received in the interior channel of the sleeve and at least a portion of the keel of the tibial component received in the relief of the sleeve;

wherein the tibial component and the sleeve are capable of being assembled in an unlocked state and in a locked state, wherein in both the unlocked and locked states at least a portion of the stem of the tibial component is received in the interior channel of the sleeve;

wherein the tibial component and the sleeve are capable of relative rotation when in the unlocked state; and wherein when the tibial component and the sleeve are in the locked state the stem of the tibial component and the sleeve frictionally interlock to prevent relative rotation between the tibial component and the sleeve.

2. The prosthetic knee system of claim 1 wherein the proximal surface of the sleeve has a generally oval shape with a major axis defining posterior and anterior portions of the proximal surface, and wherein the relief is in the posterior portion of the proximal surface of the sleeve.

3. The prosthetic knee system of claim 1 wherein the keel and relief are sized, shaped and positioned to allow relative rotation between the tibial component and the sleeve when the tibial component and the sleeve are in the unlocked state.

4. The prosthetic knee system of claim 3 wherein the keel and relief are sized, shaped and positioned to allow plus or minus twenty degrees of relative rotation between the tibial component and the sleeve when the tibial component and sleeve are in the unlocked state.

5. The prosthetic knee system of claim 1 wherein the tibial component has a plurality of spaced keels and the sleeve has a plurality of spaced reliefs in the proximal surface to receive the keels.

6. The prosthetic knee system of claim 1 wherein the tibial component has a central plane defining medial and lateral portions and the proximal surface of the sleeve has a major axis, and wherein the keel and relief are sized, shaped and positioned so that the tibial component and sleeve are capable of being frictionally locked together in a position wherein the angle between the central plane of the tibial component and the major axis of the proximal surface of the sleeve is less than 90°.

7. The prosthetic knee system of claim 1 wherein the tibial component has a central plane defining medial and lateral portions and the proximal surface of the sleeve has a major axis, and wherein the keel and relief are sized, shaped and positioned so that the tibial component and sleeve are capable of being frictionally locked together in a position wherein the angle between the central plane of the tibial component and the major axis of the proximal surface of the sleeve is 90°.

8. The prosthetic knee system of claim 7 wherein the tibial component has a central plane defining medial and lateral portions and the proximal surface of the sleeve has a major axis, and wherein the keel and relief are sized, shaped and positioned so that the tibial component and sleeve are capable of being frictionally locked together in a position wherein the angle between the central plane of the tibial component and the major axis of the proximal surface of the sleeve is less than 90°.

9. The prosthetic knee system of claim 8 wherein the tibial component has a central plane defining medial and lateral portions and the proximal surface of the sleeve has a major axis, and wherein the keel and relief are sized, shaped and positioned so that the tibial component and sleeve are capable of being frictionally locked together in a position where the angle between the central plane of the tibial component and the major axis of the proximal surface of the sleeve is between 70° and 110°.

10. A prosthetic knee system comprising:
a femoral component;
a tibial component comprising a tibial tray, a stem and a keel, the tibial tray having a distal side and an opposite side, the stem extending from the distal side of the tibial tray, the keel extending between the distal side of the tray and the stem, a majority of the opposite side of the tibial tray being planar;
a tibial bearing component having a contoured bearing side; and
a modular sleeve comprising a proximal surface with a relief, a distal end, a tapered outer surface between the proximal surface and the distal end and an interior channel extending from the proximal surface to the distal end;

wherein the keel and stem of the tibial component and interior channel and relief of the sleeve are sized, shaped and positioned to allow the sleeve to be mounted on the tibial component with at least a portion of the stem of the tibial component received in the interior channel of the sleeve and at least a portion of the keel of the tibial component received in the relief of the sleeve;

wherein the stem of the tibial component and interior channel of the sleeve are sized and shaped to allow the tibial component and the sleeve to be selectively locked together through friction to prevent rotation between the tibial component and the sleeve; and wherein the keel and the relief are sized, shaped and positioned to allow the tibial component and the sleeve to be selectively locked together in one of a plurality of orientations.

11. The prosthetic knee system of claim 10 wherein the proximal surface of the sleeve has a generally oval shape with a major axis defining posterior and anterior portions of the proximal surface, and wherein the relief is in the posterior portion of the proximal surface of the sleeve.

12. The prosthetic knee system of claim 10 wherein the keel and relief are sized, shaped and positioned to allow relative rotation between the tibial component and the sleeve when the tibial component and sleeve are not frictionally locked.

13. The prosthetic knee system of claim 12 wherein the keel and relief are sized, shaped and positioned to allow plus or minus twenty degrees of relative rotation between the tibial component and the sleeve when the tibial component and sleeve are not frictionally locked.

14. The prosthetic knee system of claim 12 wherein the tibial component has a plurality of spaced keels and the sleeve has a plurality of spaced reliefs in the proximal surface to receive the keels.

15. The prosthetic knee system of claim 10 wherein the tibial component has a central plane defining medial and lateral portions and the proximal surface of the sleeve has a major axis, and wherein the keel and relief are sized, shaped and positioned so that the tibial component and sleeve are capable of being frictionally locked together in a position wherein the angle between the central plane of the tibial component and the major axis of the proximal surface of the sleeve is less than 90°.

16. The prosthetic knee system of claim 10 wherein the tibial component has a central plane defining medial and lateral portions and the proximal surface of the sleeve has a major axis, and wherein the keel and relief are sized, shaped and positioned so that the tibial component and sleeve are capable of being frictionally locked together in a position wherein the angle between the central plane of the tibial component and the major axis of the proximal surface of the sleeve is 90°.

17. The prosthetic knee system of claim 16 wherein the tibial component has a central plane defining medial and lateral portions and the proximal surface of the sleeve has a major axis, and wherein the keel and relief are sized, shaped and positioned so that the tibial component and sleeve are capable of being frictionally locked together in a position wherein the angle between the central plane of the tibial component and the major axis of the proximal surface of the sleeve is less than 90°.

18. The prosthetic knee system of claim 17 wherein the tibial component has a central plane defining medial and lateral portions and the proximal surface of the sleeve has a major axis, and wherein the keel and relief are sized, shaped and positioned so that the tibial component and sleeve are capable of being frictionally locked together in a position where the angle between the central plane of the tibial component and the major axis of the proximal surface of the sleeve is between 70° and 110°.

* * * * *